(12) United States Patent
Guan et al.

(10) Patent No.: US 8,691,189 B2
(45) Date of Patent: Apr. 8, 2014

(54) METHOD OF COLORECTAL CANCER DETECTION BY USING RADIOLABELED ANTI-GRP78 PEPTIDE

(75) Inventors: Siao-Syun Guan, Taoyuan County (TW); Chun-Chia Cheng, Taoyuan County (TW); Shui-Cheng Lee, Taoyuan County (TW); Hsien-Ming Wu, Taoyuan County (TW)

(73) Assignee: Institute of Nuclear Energy Research, Atomic Energy Council, Lungtan, Taoyuan (TW)

( * ) Notice: Subject to any disclaimer, the term of this patent is extended or adjusted under 35 U.S.C. 154(b) by 393 days.

(21) Appl. No.: 13/026,471

(22) Filed: Feb. 14, 2011

(65) Prior Publication Data
US 2012/0207675 A1    Aug. 16, 2012

(51) Int. Cl.
*A61K 49/04* (2006.01)
*A61K 49/00* (2006.01)
*A61K 49/14* (2006.01)
*A61K 38/08* (2006.01)
*C07K 7/06* (2006.01)

(52) U.S. Cl.
CPC ............. *A61K 49/0004* (2013.01); *A61K 49/14* (2013.01); *A61K 38/08* (2013.01); *C07K 7/06* (2013.01)
USPC ......... 424/9.4; 424/1.11; 424/1.65; 424/1.69; 424/9.1; 530/303; 530/328

(58) Field of Classification Search
CPC ... A61K 51/00; A61K 2123/00; A61K 51/08; A61K 38/00; A61K 2121/00; A61K 51/0406; A61K 51/04; A61K 51/0491; A61K 39/00; A61K 49/00; A61K 49/0004; A61K 49/10; A61K 38/08; A61K 38/04; C07K 7/06; C07K 14/47488; C07K 7/00; C07K 7/04; C07F 13/00; C07F 13/005
USPC ........... 424/1.11, 1.65, 1.69, 1.81, 1.85, 1.89, 424/9.1, 9.3, 9.4, 9.5, 9.6, 9.7, 9.8; 514/1, 514/1.1; 530/300, 303, 308, 328, 329
See application file for complete search history.

(56) References Cited

U.S. PATENT DOCUMENTS

2005/0191294 A1*    9/2005    Arap et al. ................. 424/143.1

OTHER PUBLICATIONS

Golub et al, Science, 1999, vol. 286, pp. 531-537.*
Maddalo et al, Plos One, 2012, vol. 7, Issue 10, pp. 1-14.*
Gonzalez-Gronow et al, Cancer Res., 2006, vol. 66, No. 23, pp. 11424-11431.*
Hardy et al (Biochemical Pharmacology, 2008, vol. 75, pp. 891-899).*

* cited by examiner

*Primary Examiner* — D Jones
(74) *Attorney, Agent, or Firm* — Jackson IPG PLLC

(57) ABSTRACT

The present disclosure describes techniques used for colorectal cancer detection. Position and distribution of colorectal cancer tumor are detected through nuclear imaging. Alternatively, stage of colorectal cancer is identified by shading value in tumor. Thus, the present disclosure provides a safe and noninvasive clinical method for diagnosing and tracing level and distribution of colorectal cancer before and after treatment.

7 Claims, 7 Drawing Sheets

METHOD OF COLORECTAL CANCER DETECTION BY USING RADIOLABELED ANTI-GRP78 PEPTIDE

TECHNICAL FIELD OF THE DISCLOSURE

The present disclosure relates to colorectal cancer detection; more particularly, relates to detecting position and distribution of colorectal cancer tumor through nuclear imaging, or identifying stage of colorectal cancer by shading value in tumor, where the present disclosure is thus a safe and noninvasive clinical method for diagnosing and tracing level and distribution of colorectal cancer before and after treatment.

DESCRIPTION OF THE RELATED ARTS

Colorectal cancer is one of the most common cancers. Even some said it is the secondary major cause to death in the world.

Recently, happening ratio of colorectal cancer is rising. Colorectal cancer in the early stage has a five-year survival rate of more than 90% if treatment is applied before expansion of the cancer cells. But, only ⅓ of the cancer patients are found before cancer metastasis. If metastasis to lymph happens, the five-year survival rate will be reduced to about 50%. Once if metastasis to other organ happens, the five-year survival rate will be even reduced to less than 10%.

Clinically, anus finger exam, fecal occult blood test and carcinoembryonic antigen (CEA) test are used for detection, yet with many arguments on sensitivity and specificity. In addition, detection through colonoscopy takes time and patient may feel uncomfortable, even in danger of enterobrosis. However, X-ray imaging with barium (Ba) has to use colonscopy for confirming diagnosis result.

As studies show, glucose regulated protein 78 (GRP78) expresses very much in colorectal cancer cells. Hence, GRP78 can be taken as an index protein for diagnosing colorectal cancer. A traditional single-stem antibody can be radiolabeled to detect expression of GRP78 on colorectal cancer. However, because antibody may cause immune response, antibody may take a long time to reach position of tumor through the circulatory system and the patient may have to be exposed to radio nuclide for a long time too. Furthermore, the expense may be thus increased. Hence, the prior arts do not fulfill all users' requests on actual use.

SUMMARY OF THE DISCLOSURE

The main purpose of the present disclosure is to detect position and distribution of colorectal cancer tumor through nuclear imaging, or to identify stage of colorectal cancer by shading value in tumor, where the present disclosure is thus a safe and noninvasive clinical method for diagnosing and tracing level and distribution of colorectal cancer before and after treatment.

To achieve the above purpose, the present disclosure is a method of colorectal cancer detection by using radiolabeled anti-GRP78 peptide, comprising steps of: (a) obtaining an anti-peptide receptor of glucose regulated protein 78 (GRP78) of colorectal cancer; (b) obtaining a target labeled with a radioactive isotope; and (c) through intravenous injection, putting the radiolabeled substance into a human body or an animal body to process a nuclear imaging for obtaining an image of a colorectal cancer living through computed tomography, where the target has a radiolabeled substance of the anti-peptide receptor of GRP78 (anti-GRP78 peptide) labeled by the radioactive isotope; where the computed tomography is positron emission tomography (PET) or single photon emission computed tomography (SPECT); and where the radioactive isotope is a radio nuclide of Tc-99m, I-123, I-125, In-111, Re-188 or Ga-68. Accordingly, a novel method of colorectal cancer detection by using radiolabeled anti-GRP78 peptide is obtained.

BRIEF DESCRIPTIONS OF THE DRAWINGS

The present disclosure will be better understood from the following detailed description of the preferred embodiment according to the present disclosure, taken in conjunction with the accompanying drawings, in which FIG. 1 is the flow view showing the preferred embodiment according to the present disclosure.

DESCRIPTION OF THE PREFERRED EMBODIMENT

Figure 1:
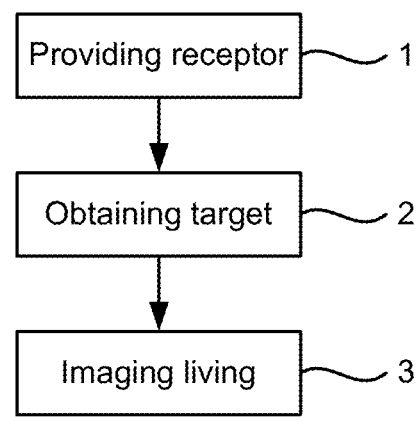
Figure 2:
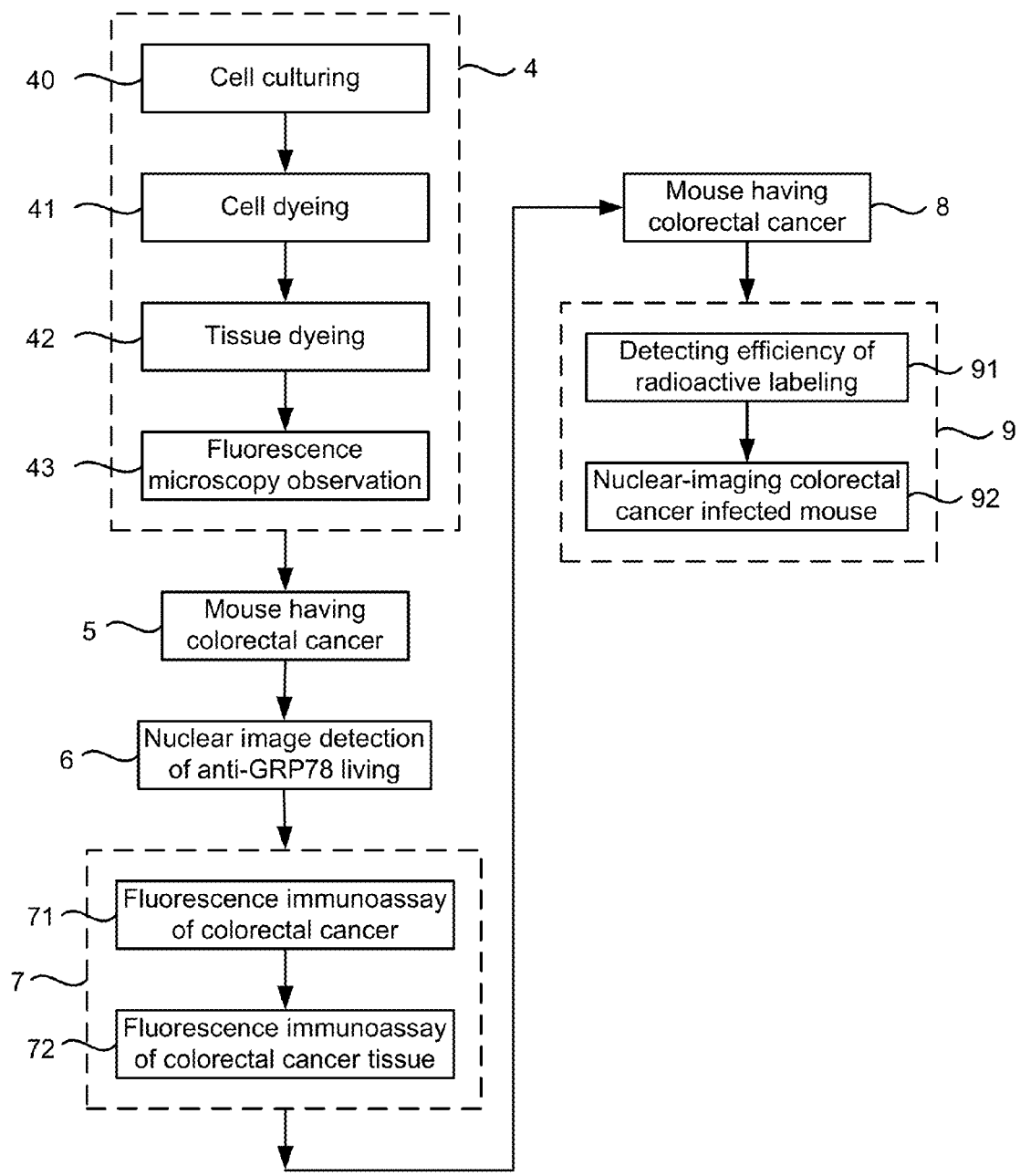
FIG. 2 is the flow view showing the confirmation of the preferred embodiment.

The following description of the preferred embodiment is provided to understand the features and the structures of the present disclosure.

FIG. 1 to FIG. 6 are a flow view showing a preferred embodiment according to the present disclosure; a flow view showing confirmation of the preferred embodiment; a view showing immunofluorescence cell staining of colorectal cancer; a view showing immunofluorescence tissue staining of colorectal cancer; a view showing labeling effects after 1 hour and 1.5 hour; and a the view showing microSPECT/CT. As shown in the figures, the present disclosure is a method of colorectal cancer detection by using radiolabeled anti-GRP78 peptide, where detection is noninvasive on taking a sample from living for diagnosing and tracing colorectal cancer before and after a treatment. The method according to the present disclosure comprises the following steps:

(a) Providing receptor 1: An anti-peptide receptor of glucose regulated protein 78 (GRP78) of colorectal cancer is provided.

(b) Obtaining target 2: A target labeled with a radioactive isotope is obtained. The target contains a radiolabeled substance of anti-peptide receptor of GRP78 (anti-GRP78 peptide) labeled by the radioactive isotope. Therein, the target is obtained by labeling the anti-GRP78 peptide with the radioactive isotope and the radioactive isotope is a radio nuclide of Tc-99m, I-123, I-125, In-111, Re-188 or Ga-68.

(c) Imaging living 3: Through intravenous injection, the radiolabeled substance is put into a human body or an animal body for processing a nuclear imaging, where an image of a colorectal cancer living is obtained through computed tomography and the computed tomography is positron emission tomography (PET) or single photon emission computed tomography (SPECT).

Thus, a novel method of colorectal cancer detection by using radiolabeled anti-GRP78 peptide is obtained.

In step (b), the radiolabeled substance of anti-GRP78 peptide labeled by the radioactive isotope is used as a target detected agent of colorectal cancer for PET or SPECT, where the target is obtained by labeling the anti-GRP78 peptide with the radioactive isotope and the radioactive isotope is a radio nuclide of Tc-99m, I-123, I-125, In-111, Re-188 or Ga-68. Thus, the target detected agent of colorectal cancer is used to diagnose and trace colorectal cancer before and after treatment.

The present disclosure is confirmed through the following steps:

(A) Immunofluorescence cell staining 4:
(A1) Cell culturing 40:
 I. A few colorectal cancer cells are cultured in a RPMI1640 of 10% fetal bovine serum (FBS) (containing 2 mM glutamine, penicillin (100 U/ml) and streptomycin (100 g/ml)).
 II. The cells are put in a culture chamber having 5% $CO_2$ at 37° C.
 III. After being fully grown, the cells adhered on culture dishes are reacted with 0.05% Trypsin and are washed down.
 IV. The cells washed down are further washed with a Hank's balanced salts solution.
 V. The washed cells are obtained at a number about $1 \times 10^4$ to be put into a chamber slide having eight individual sections for further culturing.
 VI. The cells are cultured for about 4 hours to be fully adhered with the chamber slide.
(A2) Cell dyeing 41:
 I. The cell culture medium is carefully removed and 95% alcohol is instantly added for dehydration for 1 minute.
 II. After removing alcohol, 1× normal saline solution is used for washing for 3 times.
 III. 100% acetone is added for reaction with the cells for 1 minute.
 IV. After removing acetone, 95% alcohol (having 5% acetic acid) is used for reaction at −20° C. for 5 minutes.
 V. After removing supernatant, 1:50 GRP78 antibodies or peptides are added for reaction with the cells at 4° C. overnight (about 8 hours), where the GRP78 antibodies or peptides are labeled with a fluorescent material of fluorescein isothiocyanate (FITC).
 VI. After removing supernatant, 1× normal saline solution is used for washing for 3 times and a de-ionized water ($d2H_2O$) is further used for washing for the last time.
 VII. The chamber slide is put into a constant temperature chamber to be dried.
(A3) Tissue dyeing 42:
 I. Sliced tissues of colorectal cancer are obtained through a freezing microtome at −20° C.
 II. The sliced tissues have a thickness of 10 micrometers (μm).
 III. The sliced tissues are dehydrated with alcohol to ratios of 70% (30 seconds), 85% (30 seconds) and 95% (30 seconds).
 IV. The sliced tissues are put into a constant temperature chamber for drying for 2 minutes.
 V. The sliced tissues are separately added with anti-GRP78 peptide labeled with FITC (anti-GRP78-FITC, 1:100 diluted), pure anti-GRP78 peptide and pure FITC for reaction at 4° C. overnight.
 VI. The sliced tissues are washed with a normal saline solution for 3 times each time for 5 minutes.
(A4) Fluorescence microscopy observation 43:
 I. The sliced tissues are fully dried for observation with a microscope.
 II. A filter set is adjusted under excitation of a blue light emitted with a wavelength of 518 nm±30 nm.
 III. A fluorescence image is captured with a digital camera device.
 IV. An image of the cells is captured under a visible light as a reference to the fluorescence image.
(B) Mouse having colorectal cancer 5:
(B1) A mouse (BABL/c) is obtained.
(B2) A number of colorectal cancer cells (CT26) are put into the rare right leg of the mouse through subcutaneous injection, where the number of CT26 is $1 \times 10^6$.
(B3) The colorectal cancer cells are grown subcutaneously for 3~4 weeks to obtain a bulge about 1~1.5 $cm^3$ high.
(C) Nuclear image detection of anti-GRP78 living 6:
(C1) 3 mL of a normal saline solution is used to wash out 188Re at an amount about 1.5-2 mL.
(C2) 1 mL of 188Re solution is dissolved with a powder of 50 mg Glucohepatonate and 5 mg stannous chloride.
(C3) The powder is fully dissolved through shaking for 15 minutes.
(C4) A solution having 30 μL of anti-GRP78 peptide is added (each 2 mg contains 50% DMSO).
(C5) Reaction is processed at a room temperature for 1 hour.
(C6) 2 L of the solution is obtained to be dotted on a chromatography paper of instant thin-layer chromatography silica gel (ITLC-SG) for labeling.
(C7) After 15 minutes, 100 μL of blood having the labeled peptide is injected into the mouse having colorectal cancer and, then, nuclear imaging is processed through microSPECT/CT after 4 hours.

Figure 3:
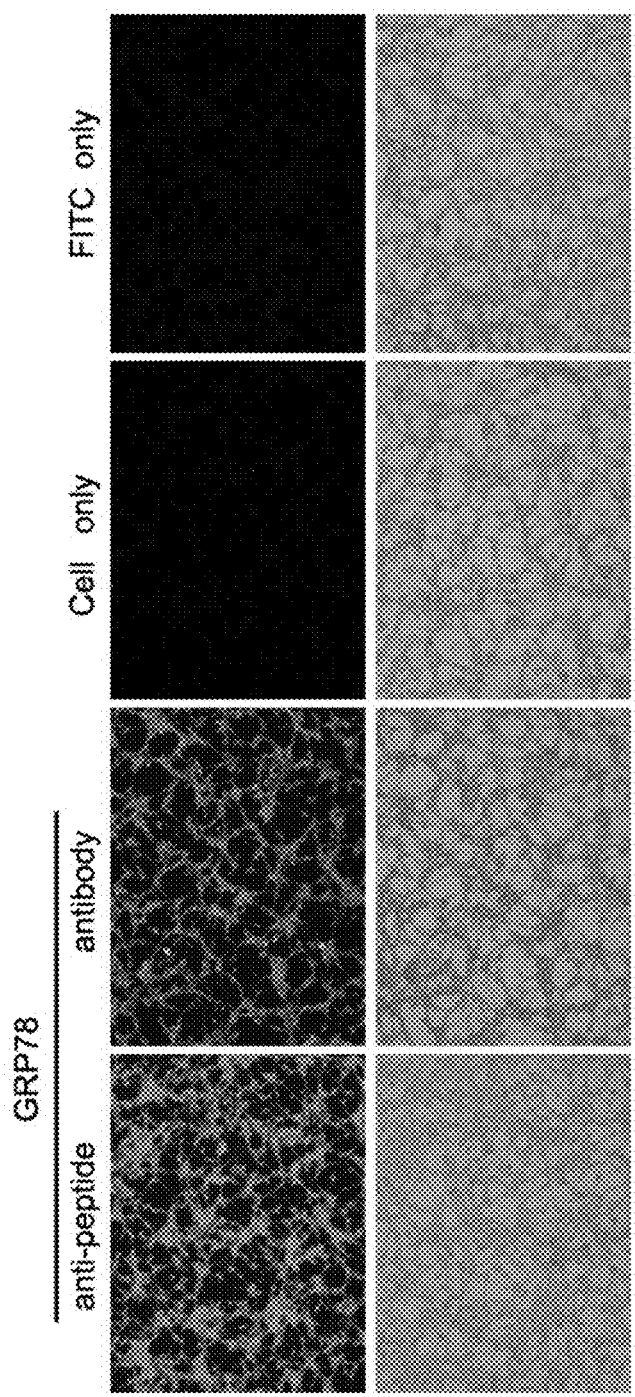
FIG. 3 is the view showing the immunofluorescence cell staining of colorectal cancer.

A result of the above steps is as follows:
(A) Fluorescence immunoassay 7:
(A1) Fluorescence immunoassay of colorectal cancer 71:
As modern studies show, colorectal cancer cells and tissues show a lot of GRP78. The present disclosure uses the anti-GRP78-FITC to detect colorectal cancer cells for acquiring ability of anti-GRP78-FITC on detecting expression of GRP78. In FIG. 3, only the anti-GRP78 peptide is able to detect the expression of GRP78; a reaction of a GRP78 antibody to a colorectal cancer cell is used as a reference to show that the anti-GRP78 peptide still has obvious fluorescence expression; and, pure colorectal cancer cells or colorectal cancer cells reacted with the pure FITC shows no fluorescence expression. As a result, the anti-GRP78 peptide is able to detect expression of GRP78 in colorectal cancer cell.

Figure 4:
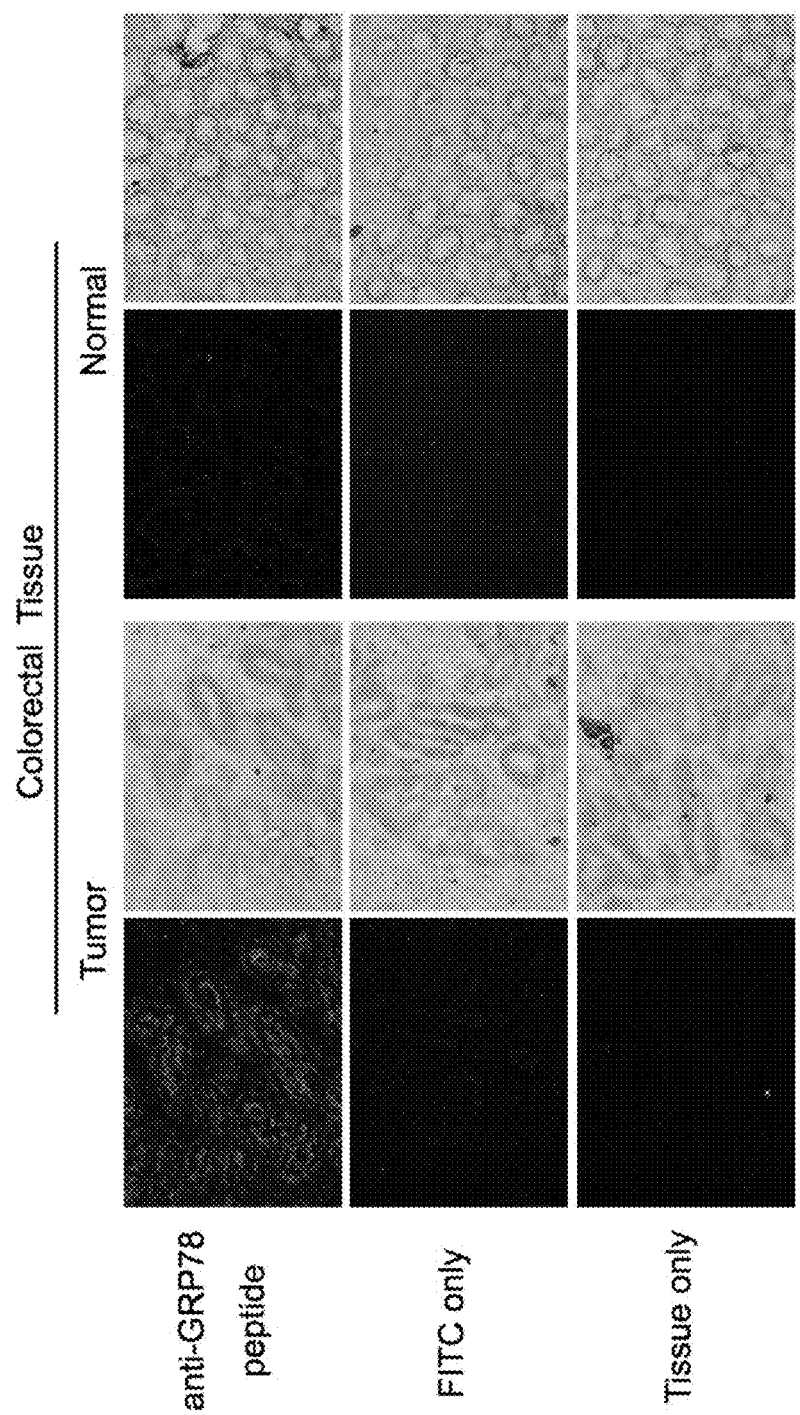
FIG. 4 is the view showing the immunofluorescence tissue staining of colorectal cancer.

(A2) Fluorescence immunoassay of colorectal cancer tissue 72:
Then, the colorectal cancer tissues are analyzed to acquire performance of the anti-GRP78-FITC on detecting GRP78 expression in colorectal cancer tissue. A normal set and a set of colorectal cancer tissues are used for comparison. The colorectal cancer tissues are dyed in three ways: one is dyed with the anti-GRP78-FITC, where one is dyed with the pure FITC and one a tissue having no antibody or fluorescence material. In FIG. 4, the anti-GRP78-FITC is able to detect GRP78 expression in colorectal cancer tissue.

Figure 5A:
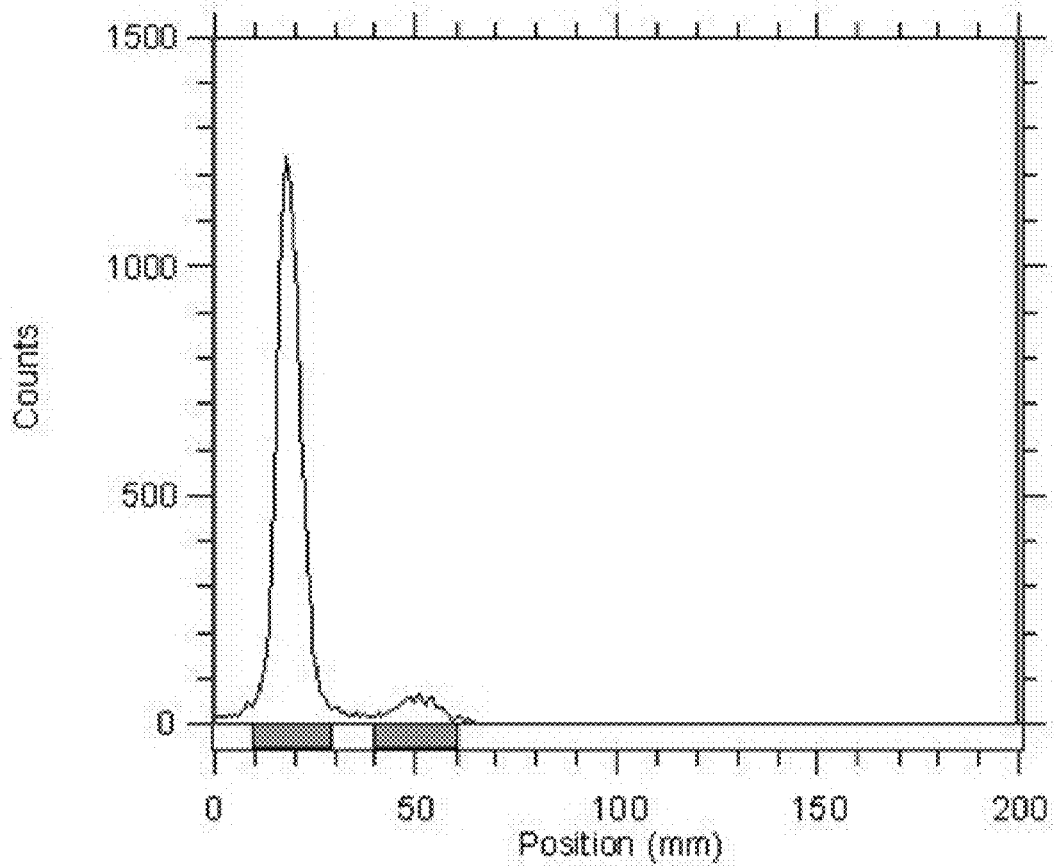
FIGS. 5A and 5B are the charts showing the labeling effects after 1 hour and 1.5 hour.
Figure 5B:
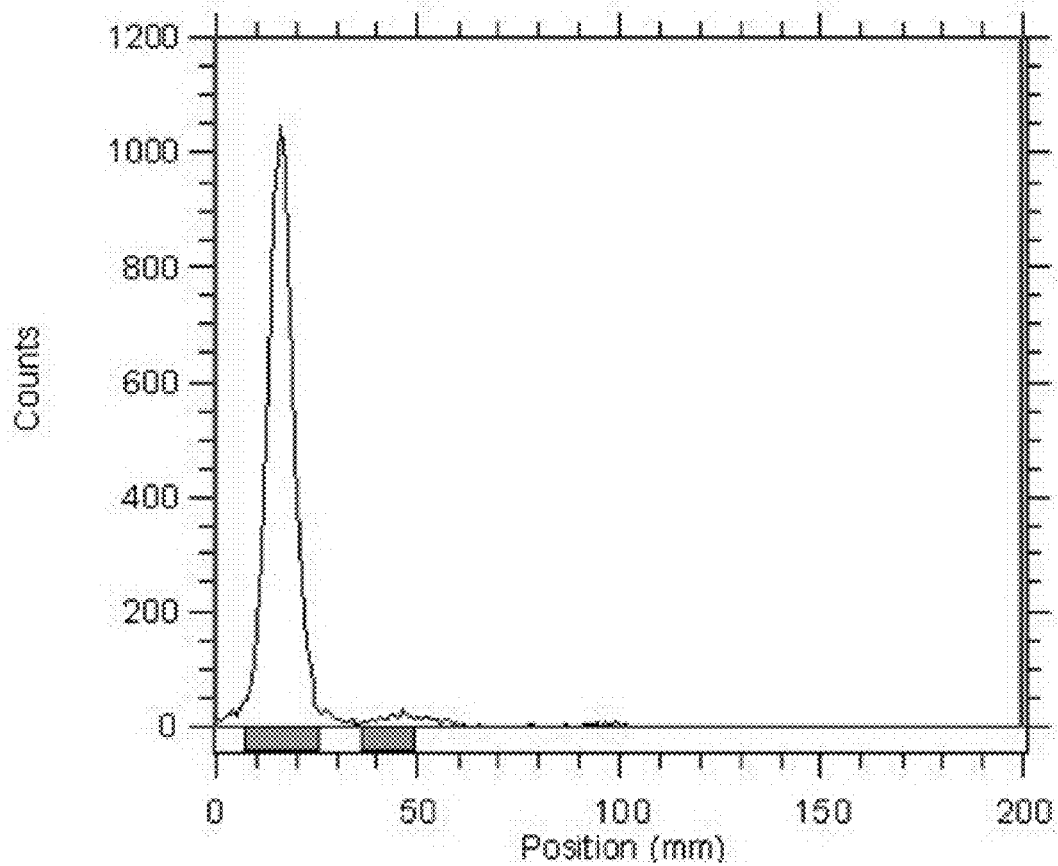
Figure 6:
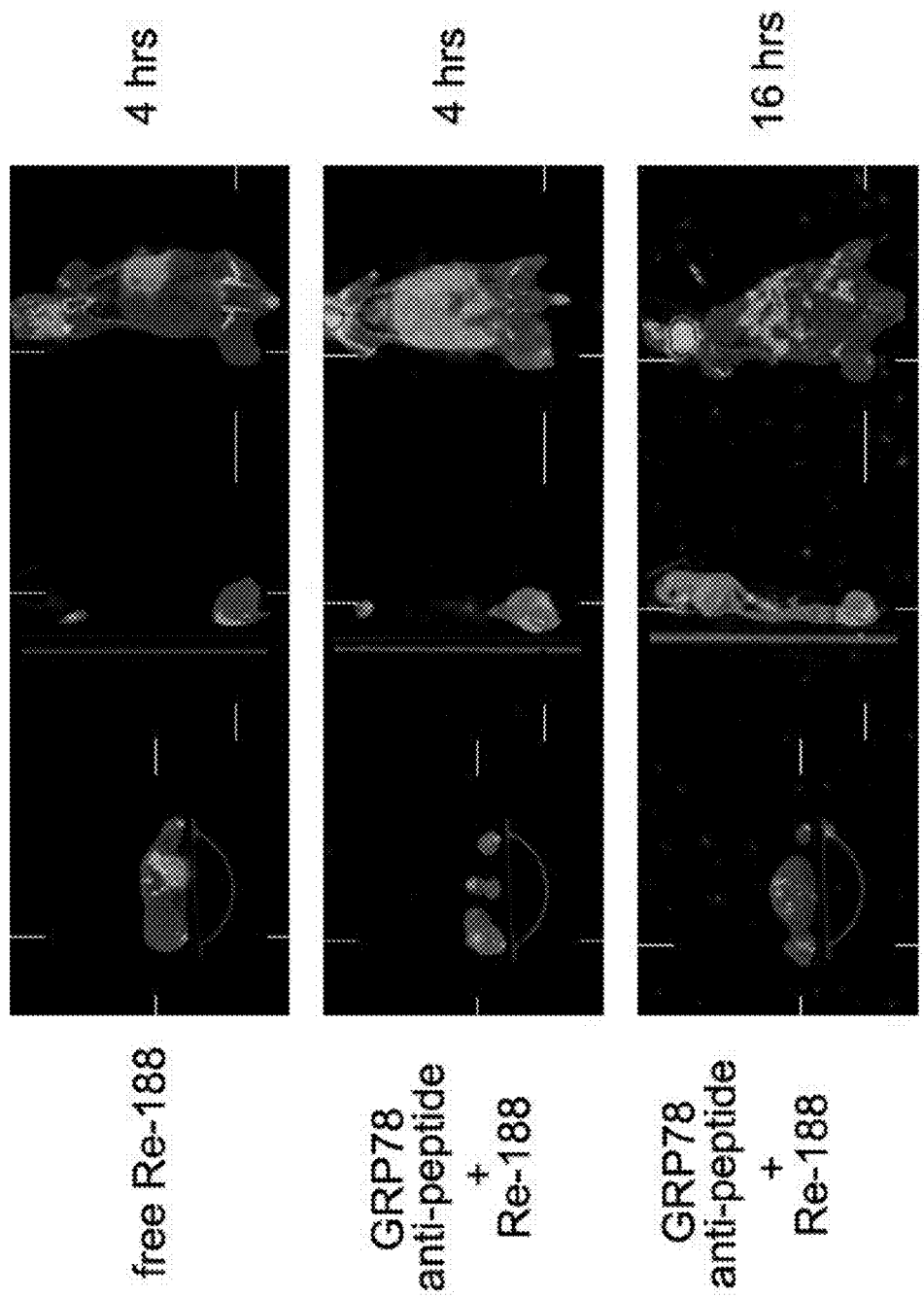
FIG. 6 is the view showing the microSPECT/CT.

(B) Mouse having colorectal cancer 8:
The colorectal cancer cells (CT26) are vaccinated into the leg of the mouse to obtain the bulge (about 1~1.5 $cm^3$ high) after 3 weeks for building a mouse model for nuclear imaging.
(C) Nuclear image detection of anti-GRP78 living 9:
(C1) Detecting efficiency of radioactive labeling 91:
For acquiring a reliable nuclear image, radioactive labeling efficiency is critical. In FIG. 5A and FIG. 5B, both the left peaks represent mixtures of peptide labeled with a radioactive material (anti-GRP78-188Re); and both the right peaks represent free Re-188. As results show, about 92% of radioactive labeling efficiency is achieved after 1 hour (in FIG. 5A); and, 97% of radioactive labeling efficiency is achieved after 1.5 hour (in FIG. 5B).

(C2) Nuclear-imaging colorectal cancer infected mouse 92:

For acquiring detecting effect of the anti-GR78-188Re on living, the mouse is analyzed through microSPECT/CT (in FIG. 6) and show that radio signals are obtained on the cancer bulge at the leg after being injected with the anti-GRP78-188Re for 4 hours, while the signals are not obviously increased after 18 hours.

Conclusively, step (a) is processed for culturing cells and confirming effect of anti-GRP78 peptide; step (b) is for building animal model by injecting the cells into an animal; and, step (c) is for imaging colorectal cancer cells of the animal. These three steps are continuous to label anti-GRP78 peptide with radioactive material for imaging a living.

Hence, the present disclosure has the following advantages:

(1) The present disclosure provides a radiolabeled anti-GRP78 peptide molecular targeted detected agent and related nuclear medicine imaging for detecting level and distribution of colorectal cancer. Hence, the present disclosure is a safe and noninvasive clinical method for diagnosing and tracing level and distribution of colorectal cancer before and after treatment.

(2) A GRP78 receptor specific to colorectal cancer is provided, where its anti-peptide (whose amino acid sequence is Tyr-Ile-Phe-Pro-Tyr-Ile-Glu-Leu-Cys (SEQ ID NO:1) is used to be labeled with a radio nuclide of Tc-99m, I-123, Re-188 or Ga-68 for nuclear imaging of colorectal cancer tumor.

(3) A method is provided to detect existence, position and distribution of colorectal cancer through nuclear imaging; or, to further identify stage of colorectal cancer with shading value in nuclear image.

(4) The present disclosure uses radiolabeled peptide with the following advantages:

I. Small size: Size of peptide is about 1 kDa with an acute amino acid sequence.

II. Easy fabrication: Peptide can be manually fabricated with more than 30 amino acid contained within.

III. Easy labeling: Because the molecular structure is acute, amino acid composition can be self-designed for nuclear medicine and for enhancing labeling efficiency.

IV. Various labeling methods: A number of labeling methods can be chosen, including direct labeling and indirect labeling with chelating substance.

V. Tolerance to chemical modification or radioactive labeling: Peptide is merely composed of amino acids and amino acids are covalently bond in between. Thus, the structure is not easily destroyed and tolerance to reaction environment is improved.

VI. Bondage with chelating agent: Since amino acid sequence of peptide can be freely re-designed, N-end or C-end of peptide has ability to be bonded with chelating agent (bifunctional chelating agent, BFCA) for obtaining stable status.

VII. Fast exclusion: Because peptide molecule is smaller than antibody for 100-150 times, it can be easily excluded from its position in blood or in non-tumor tissue for enhancing image signals of tumor or specific bonding position.

VIII. Good tumor-to-background ratio: Once the probe in non-tumor position is fast excluded, signal ratio of tumor position to non-tumor position (blood or other organ) is enhanced. Relatively, activity of radioactive ray can be decreased for reducing explosion amount to human body.

IX. Good penetration: Because tumor tissue is loose, small peptide can be easily penetrated into tumor cells for obtaining tumor position and for treatment with less harm to normal cell.

X. Low toxicity: Peptide is composed of amino acid only and, so, is low in toxicity.

XI. Low immunogenicity: Because of the small size, low identification to immune cells is obtained and thus immune reaction is prevented.

XII. High affinity and specificity to receptor: Because the bonding position of antigen to antibody is decided by a few amino acid sequences but not the entire antibody molecule, the peptide thus has high affinity and specificity for its composition of these amino acid sequences.

To sum up, the present disclosure is a method of colorectal cancer detection by using radiolabeled anti-GRP78 peptide, where position and distribution of colorectal cancer tumor are detected through nuclear imaging, or stage of colorectal cancer is identified by shading value in tumor; and where the present disclosure is thus a safe and noninvasive clinical method for diagnosing and tracing level and distribution of colorectal cancer before and after treatment.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A method of colorectal cancer detection by using radiolabeled anti-GRP78 peptide, the method comprising:
    obtaining an anti glucose regulated protein 78 (GRP78) peptide;
    labeling the anti-GRP78 peptide with a radioactive isotope to obtain a target,
    injecting said target into a body selected from a group consisting of a human body or an animal body to process a nuclear imaging; and
    obtaining an image of a colorectal tissue through computed tomography, wherein binding of said target to colorectal tissue detects colorectal cancer, wherein an anti-GRP78 peptide is a peptide that binds to GRP78, wherein the anti-GRP-78 peptide has the amino acid sequence Tyr Ile Phe Pro Tyr Ile Glu Leu Cys (SEQ ID NO:1).

2. The method according to claim 1, wherein said computed tomography is selected from a group consisting of positron emission tomography (PET) and single photon emission computed tomography (SPECT).

3. The method according to claim 1, wherein said target is obtained through labeling said anti-GRP78 peptide with said radioactive isotope, and wherein said radioactive isotope is a radio nuclide selected from a group consisting of Tc-99m, I-123, I-125, In-111, Re-188 and Ga-68.

4. The method according to claim 1, wherein said target, which has a substance labeled by said radioactive isotope, is a target detected agent of colorectal cancer.

5. The method according to claim 1, wherein said target is labeled with said radioactive isotope to be processed through a tomography selected from a group consisting of PET and SPECT.

6. The method according to claim 4, wherein said target is processed through a radioactive isotope labeling method to label anti-peptide of GRP78 of colorectal cancer cell with a radio nuclide selected from a group consisting of Tc-99m, I-123, I-125, In-111, Re-188 and Ga-68.

7. The method according to claim 4, wherein said target detected agent diagnoses and traces colorectal cancer before and after treatment.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Anti-GRP78 Peptide

<400> SEQUENCE: 1

Tyr Ile Phe Pro Tyr Ile Glu Leu Cys
1               5
```